United States Patent [19]

Brooks

[11] Patent Number: 4,924,877

[45] Date of Patent: May 15, 1990

[54] PRESSURE SENSING CATHETER

[75] Inventor: Albert E. Brooks, Carpinteria, Calif.

[73] Assignee: Ambrook Medical Concepts, Inc., Carpinteria, Calif.

[21] Appl. No.: 276,269

[22] Filed: Nov. 25, 1988

[51] Int. Cl.⁵ .............................................. A61B 5/00
[52] U.S. Cl. ................................... 128/748; 128/667; 128/673
[58] Field of Search ................... 128/748, 664–667, 128/672–675, 778, 780; 604/101–103; 73/705, 708, 715

[56] References Cited

U.S. PATENT DOCUMENTS

| 3,686,958 | 8/1972 | Porter et al. | 128/748 X |
| 3,789,667 | 2/1974 | Porter et al. | 128/748 X |
| 4,543,961 | 10/1985 | Brown | 128/748 X |
| 4,611,600 | 9/1986 | Cohen | 128/748 X |
| 4,711,249 | 12/1987 | Brooks | 128/748 |

Primary Examiner—Angela D. Sykes
Attorney, Agent, or Firm—Donald D. Mon

[57] ABSTRACT

A pressure sensing catheter includes a pressure sensor within the length of a hollow catheter insertable into the human body. The catheter has a surrounding circumferential pressure transmitting membrane that is exposed to the region whose pressure is being measured. The membrane bears against a cantilevered shutter whose excursion into a gap in an optical fiber varies the amount of light transmitted by the fiber as a function of the external pressure.

6 Claims, 1 Drawing Sheet

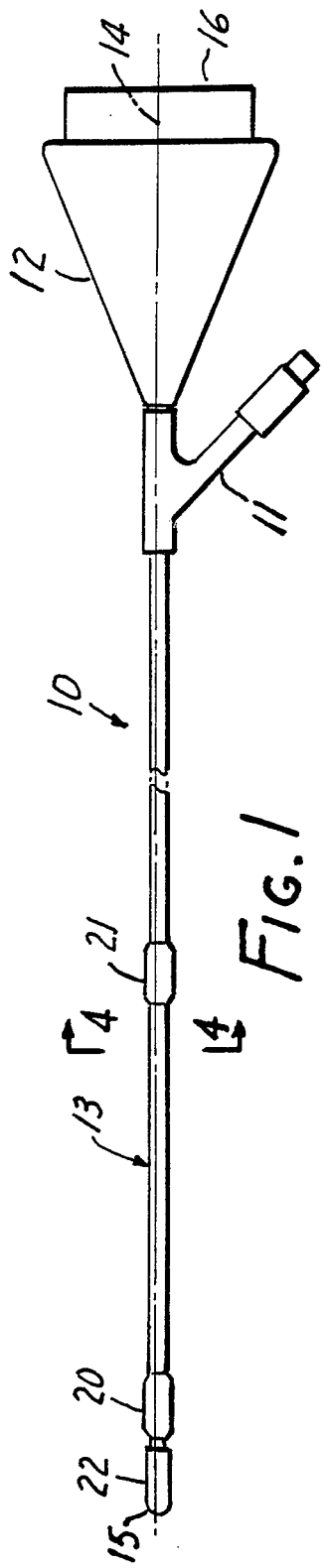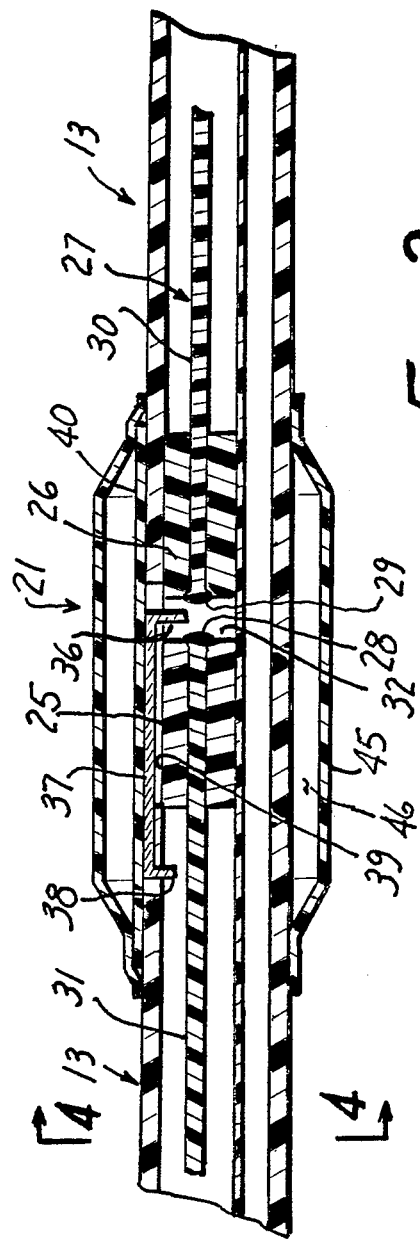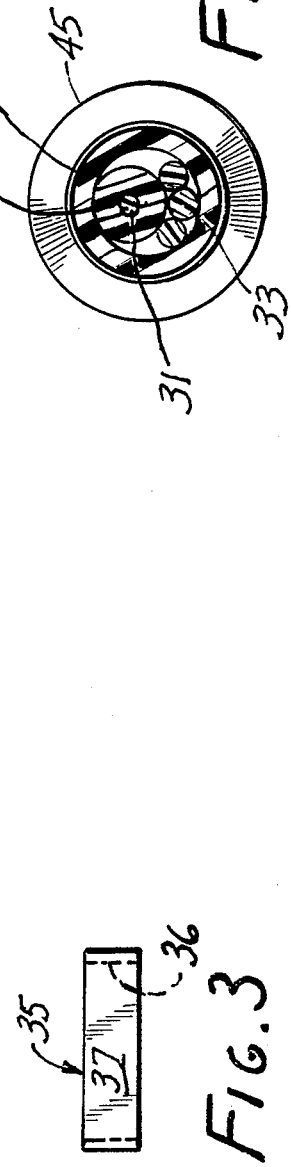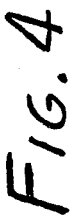

4,924,877

PRESSURE SENSING CATHETER

FIELD OF THE INVENTION

This invention relates to catheters utilized in the measurement of pressures in the human body such as in the bladder, in the urethra, and in the uterus.

BACKGROUND OF THE INVENTION

This invention relates to pressure sensing catheters of the type having a substantial length to be inserted into the human body to measure pressures therein. It finds its best potential use at this time in the measurement of pressure in the bladder and in the urethra and in measurement of intrauterine pressure in obstetrical procedures.

Catheters for these purposes are known. Some of them require the presence of an electrical current in the instrument within the human body and are therefore objectionable on that ground alone. All are sensitive to their angular orientation within the region being measured and therefore have certain latent uncertainties in their output. Others suffer from excessive cost due to their complexity. It should be recalled that these are small catheters. In general, the outer diameter of this basic catheter structure is only about 0.080 inches and it is necessary to keep the diameter of the instrument at its largest within about 0.150 inches. Thus, the device is quite small and is difficult to manufacture whatever its construction.

It is an object of this invention to utilize only light internally of the human body for sensing and to provide the catheter and its sensor in a form which is economically manufacturable.

BRIEF DESCRIPTION OF THE INVENTION

A pressure sensing catheter according to this invention includes a pressure sensor that is adapted to be included in the length of a hollow catheter insertable into the human body. It has a surrounding circumferential pressure transmitting membrane that is exposed to the region whose pressure is being measured. In turn this is transmitted to a pressure membrane which in turn bears against a cantilevered shutter whose excursion into a gap in an optical fiber varies the amount of light transmitted by the fiber as a function of the external pressure. The transmitted light thereby becomes a means for measuring the pressure.

A catheter according to this invention includes a length of fiber for transmitting the light and a length for returning the light, the gap being formed in the return segment of the fiber.

This construction is readily and economically manufactured to the close tolerances and small sizes required for catheters of this type.

The above and other features of this invention will be fully understood from the following detailed description and the accompanying drawings, in which:

BRIEF DESCRIPTION OF THE DRAWINGS

FIG. 1 is a side elevation of a catheter system according to this invention;

FIG. 2 is a fragmentary axial cross section of the sensor according to this invention;

FIG. 3 is a top view of a shutter in FIG. 3; and

FIG. 4 is a cross section taken at line 4—4 in FIG. 1.

DETAILED DESCRIPTION OF THE INVENTION

In FIG. 1, there is shown a catheter assembly 10 according to the invention which includes a handle 11 with conventional connections for water and carbon dioxide as necessary, together with an electronics package 12 including a light source. The cathether includes an extended flexible tube 13 having a longitudinal axis 14, a distal end 15 and a proximal end 16. For many applications, measurement of pressure at only one place along its length will be desired but in others, measurement at more than one place may be required. For example, there is shown in FIG. 1 a pair of sensors 20, 21 spaced approximately six cm apart which in the female is the approximate distance between the urethra and the bladder. It is frequently desirable to measure these two pressures simultaneously and separately from one another and this invention enables it to be done.

An end cap 22 is provided to close the distal end and provide a means for turning around the optical fiber yet to be described.

It will be observed that the device in operation will be thrust into the appropriate region of the body. Measurements of pressure will be made at the location where the sensors are placed.

Sensors 20 and 21 are identical to one another so that only sensor 21 will be described in detail. It is intended to be incorporated into the length of the flexible tube where it forms a rather short length of relative stiffness. The length of the sensor is on the order of 0.300 inches and its greatest diameter will ordinarily be on the order of about 0.140 inches which can be compressed to a dimension considerably smaller.

The flexible tube will be of the usual materials known for use in catheters. The sensor begins from its central point at a pair of mounts 25, 26 which receive the ends of an otherwise continuous optical fiber 27, usually an organic plastic fiber which can be polished to a near flatness or to a somewhat lensatic structure shown by surfaces 28, 29. The mounts and these ends are seated within the flexible tube. They represent the continuation of fiber segment 30 which goes to the end cap and is bent to return to the gap. Light sent into segment 30 will be returned to segment 31, and passed through the gap 32 to segment 33 whose intensity is measured and compared to the intensity of the original light supplied as a measurement of the pressure.

A shutter 35 comprises a body manufactured from stainless steel shimstock preferably on the order of about 0.001 inches thick. A shutter segment 36 depends from a cantilever segment 37 which has an anchor flange 38 passed through a slit in the flexible tube. A clearance slot 39 enables the cantilever segment to be bent so the shutter segment variably occludes the region of gap between the two fiber segments 31 and 33.

A pressure membrane 40 is laid atop the shutter and bears against it. In fact, it may be adhered thereto if desired although this will not usually be required. Although the pressure membrane can be laid accross it and not form a continuous tube, it is possible instead for this membrane to be modified so as to form a continuous tube surrounding the device, and this will be a convenient means to assemble it. In whatever event, the pressure membrane is stretched rather tautly across its length so as to form a springy resistance to external pressure together with the springiness of the shutter itself.

It is not desirable for this device to be sensitive to pressures from only one portion of its periphery. For this reason, a circumferential pressure transmitting membrane 45 is formed around the device and adhered to the catheter's flexible tube at ends spaced from the gap. A chamber 46, which is most conveniently filled with air at the time of assembly or which may later be filled instead with a liquid, completely surrounds the tube so that forces from any direction will affect its internal pressure that will in turn be transmitted to the internal membrane.

It will now be seen that from whatever part of the periphery the forces are exerted the pressure will be transmitted to the membrane 40 and thence to the shutter. The higher the pressure, the more light will be occluded and the transmitted light intensity can be used as means for measuring of the pressure.

The sensor 20 is identical to sensor 21. As can be seen in FIG. 4, both sensors will require a segment for conducting light to the distal end around its bend and back to their respective gaps and thence to the measurement instrument at the handle.

This construction is readily manufacturable. The membranes can all be formed conveniently to their desired dimensions and the shutter itself can be manufactured from shimstock whose properties can closely be controlled in routine manufacture. It is surprising to see the high repeatability between successively manufactured parts of this device. This device can readily be put together by reasonably skilled technicians at a greatly reduced cost compared to conventionally known devices. It requires no use of electrical currents inside the body and in general can be conveniently manufactured to its small dimensions.

This invention is not to be limited by the embodiments shown in the drawings and described in the description which are given by way of example and not of limitation, but only in accordance with the scope of the appended claims.

I claim:

1. A sensor for a pressure sensing catheter, said sensor having a longitudinal axis and a periphery, a first and a second optical fiber segment having light transmitting faces spaced from one another across a gap, a shutter having a shutter segment projecting into said gap between said faces, and also having a cantilever segment anchored to the sensor at one end, with said shutter segment projecting laterally therefrom at its other end and flexibly deflectable to move said shutter segment variably into said gap as a consequence of said deflection; a pressure membrane laid atop the cantilever segment and closing said gap; and a circumferential pressure transmitting membrane extending fully around the catheter on both sides of said gap, and enveloping a chamber filled with fluid between said membranes, said circumferential pressure transmitting membrane being normally spaced from said pressure membrane.

2. A sensor according to claim 1 in which said cantilever segment has a substantial area in contact with said pressure membrane.

3. A sensor according to claim 2 in which said cantilever segment is stiffly flexible.

4. In combination: a sensor according to claim 1 and a flexible catheter tube having a proximal end and a distal end, said tube having a slot therein to accommodate said shutter segment, and incorporating said sensor within its length.

5. A combination according to claim 4 in which a plurality of said sensors is included in the length of said catheter tube.

6. A combination according to claim 4 in which an optical fiber is carried in said catheter tube to its distal end, where it bends to form a segment leading to said gap.

* * * * *